United States Patent [19]

Temple et al.

[11] 4,431,805

[45] Feb. 14, 1984

[54] PYRIDO[2,3-D]-PYRIMIDINES

[75] Inventors: Carroll G. Temple; John A. Montgomery; Robert D. Elliott, all of Birmingham, Ala.

[73] Assignee: Southern Research Institute, Birmingham, Ala.

[21] Appl. No.: 338,542

[22] Filed: Jan. 11, 1982

Related U.S. Application Data

[63] Continuation-in-part of Ser. No. 305,907, Sep. 25, 1981, abandoned.

[51] Int. Cl.$^3$ ............... C07D 471/04; A61K 31/505; C07D 487/04
[52] U.S. Cl. .................................. 544/279; 544/323; 424/251
[58] Field of Search .......................................... 544/279

[56] References Cited

U.S. PATENT DOCUMENTS 3,288,792  11/1966  Hitchings et al. ................... 544/279

OTHER PUBLICATIONS

Hurlbert et al., J. Med. Chem., 11, 708, (1968).
Arnold, Z., Coll. Czech. Chem. Commun., 26, 3051, (1961).
Mulvery et al., J. Org. Chem., 29, 2903, (1964).
Stark et al., Tetrahedron, 29, 2209.
Watner et al., J. Org. Chem., 29, 2674, (1964).
Tseng, C. P., "Studies in Heterocyclic Chemistry", 171-185, (1979).
Elslagr et al., "Lectures in Heterocyclic Chem.", 2, S-97, S-119, -S-121, (1974).
Arnold et al., Coll. Czech. Chem. Commun., 25, 1318, (1960).
Hurst, D. T., "An Introduction to the Chemistry and Biochemistry of Pyrimidines, Purines and Pteridines", John Wiley and Sons, Ltd., 231, (1980).
Temple et al., "Synthesis of Potential Anticancer Agents", Report 85, pp. 1 and 2, (1966), Report 86, pp. 8 and 10, (1967).
Tseng, C. P., Dissertation Abstracts Int. B., 40, 3752, (1980).
Spinivasan et al., J. Org. Chem., 45, 3746, (1980).
Smith et al., Biochemistry, 20, 1241, (1981).
Grivsky et al., J. Med. Chem., 23, 327, (1980).
Bennett et al., J. Med. Chem., 24, 382, (1981).
Robins et al., J. Am. Chem. Soc. 77, 2256, (1955).
Bernetti et al., J. Org. Chem., 27, 2863, (1962).
Rizkalla et al., J. Org. Chem., 37, 3980, (1972).
Calvert et al., Europ. J. Cancer, 16, 713, (1980).
Scanlon et al., Mol. Pharmacol., 16, 261, (1979).
Bird et al., Mol. Pharmacol., 6, 573, (1970).
Irwin et al., Advan. Heterocycl. Chem., 10, 149, (1969).

*Primary Examiner*—Donald G. Daus
*Assistant Examiner*—S. A. Gibson
*Attorney, Agent, or Firm*—Roylance, Abrams, Berdo & Goodman

[57] ABSTRACT

There is disclosed a novel intermediate useful in the preparation of pyrido[2,3-d]pyrimidines, which includes N-[4- [(2-amino-4(3$\underline{H}$)-oxopyrido[2,3-d]pyrimidin-6-yl)methylamino]benzoyl]-L-glutamic acid (5-deazafolic acid), N-[4-[[(2-amino-4(3$\underline{H}$)-oxopyrido[2,3-d]-pyrimidin-6-yl)methyl]methylamino]benzoyl]-L-glutamic acid (5-deaza-N$^{10}$-methylfolic acid), N-[4-[(2,4-diaminopyrido[2,3-d]pyrimidin-6-yl)methylamino]benzoyl]-L-glutamic acid (5-deazaaminopterin), and N-[4-[[(2,4-diaminopyrido[2,3-d]pyrimidin-6-yl)methyl]methylamino]benzoyl]-L-glutamic acid (5-deazamethotrexate). This intermediate is the compound 2,4-diaminopyrido[2,3-d]pyrimidine-6-carboxaldehyde.

1 Claim, No Drawings

PYRIDO[2,3-D]-PYRIMIDINES

CROSS-REFERENCE TO RELATED APPLICATON

This application is a continuation-in-part of our copending application Ser. No. 305,907, filed Sept. 25, 1981 abandoned.

BACKGROUND OF THE INVENTION

This invention relates to an intermediate useful in the preparation of pyrido[2,3-d]pyrimidines, which includes N-[4-[(2-amino-4(3H)-oxopyrido[2,3-d]pyrimidin-6-yl)methylamino]benzoyl]-L-glutamic acid (5-deazafolic acid), N-[4-[[(2-amino-4(3H)-oxopyrido-[2,3-d]-pyrimidin-6-yl)methyl]methylamino]benzoyl]-L-glutamic acid (5-deaza-$N^{10}$-methylfolic acid), N-[4-[(2,4-diaminopyrido[2,3-d]-pyrimidin-6-yl)methylamino]benzoyl]-L-glutamic acid (5-deazaaminopterin), and N-[[(2,4-diaminopyrido[2,3-d]pyrimidin-6-yl)methyl]-methylamino]benzoyl]-L-glutamic acid (5-deazamethotrexate). This intermediate is the compound 2,4-diaminopyrido[2,3-d]pyrimidine-6-carboxaldehyde. This invention also relates to a process for using said intermediate; to the novel compounds 5-deazamethotrexate and 5-deaza-$N^{10}$-methylfolic acid; and to methods for preparing such novel compounds.

Powerful dihydrofolate reductase inhibitors such as aminopterin and methotrexate are known folic acid antagonists useful in the suppression and treatment of actue leukemia and related conditions. They have as their principal mechanism of action a competitive inhibition of the enzyme dihydrofolate reductase. Folic acid and its 7,8-dihydro derivative must be reduced to tetrahydrofolic acid by this enzyme in the process of DNA synthesis and cellular reproduction. Compounds having antifolate activity such as aminopterin and methotrexate inhibit the reduction of both folic acid and 7,8-dihydrofolic acid and interfere with tissue-cell reproduction.

Several types of quinazolinyl (5,8-dideazapteridinyl) analogs of folic acid, aminopterin, and methotrexate were reported to be inhibitors both of dihydrofolate reductase and thymidylate synthetase [A. H. Calvert, T. R. Jones, P. J. Dady, B. Grzelakowska, R. M. Paine, G. A. Taylor and K. R. Harrap, Europ. J. Cancer, 16, 713 (1980); K. J. Scanlon, B. A. Moroson, J. R. Bertino and J. B. Hynes, Mol. Pharmacol., 16, 261 (1979); O. D. Bird, J. W. Vaitkus and J. Clarke, Mol. Pharmacol., 6, 573 (1970)]. Recently, N-[4-[N-[(2-amino-4-hydroxy-6-quinazolinyl)methyl]prop-2-ynylamino]benzoyl]-L-glutamic acid (5,8-dideaza-10-propargylfolic acid) was identified as a potent inhibitor of thymidylate synthetase [T. R. Jones, A. H. Calvert, A. L. Jackman, S. J. Brown, M. Jones and K. R. Harrap, Europ. J. Cancer, 17, 11 (1981)]. This enzyme catalyzes the de novo synthesis of thymidine nucleotidase, which are required for DNA synthesis.

The synthesis of derivatives of the pyrido[2,3-d]pyrimidine ring system has been reviewed by W. J. Irwin and D. G. Wibberley, Advan. Heterocycl. Chem., 10, 149 (1969), which covers the literature to the beginning of 1968. Although many methods are reported in this review, major routes to this ring system include the cyclization of the functional derivatives of 2-aminonicotinic acids with various reagents [e.g., R. K. Robins and G. H. Hitchings, J. Am. Chem. Soc., 77, 2256 (1955)], and the reaction of derivatives of 4-aminopyrimidine with 1,3-dicarbonyl comounds or their masked derivatives [e.g., B. S. Hurlbert and B. F. Valenti, J. Med. Chem., 11, 708 (1968)]. The condensations of 4-aminopyrimidines with malondialdehyde derivatives to give pyrido[2,3-d]pyrimidines are reported by R. Bernetti, F. Mancini and C. C. Price, J. Org. Chem., 27, 2863 (1962), and B. S. Hurlbert and B. F. Valenti, J. Med. Chem., 11, 708 (1968). A procedure for the preparation of 5-oxo-(8H)-pyrido[2,3-d]pyrimidines was reported by B. H. Rizkalla and A. D. Broom, J. Org. Chem., 37, 3980 (1972). This reference discloses the following compound.

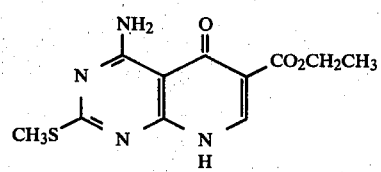

The development of procedures for the conversion of the above compound to N-[4-[(2,4-diamino-5-oxo(8H)-pyrido[2,3-d]pyrimidin-6-yl)-methylamino]benzoyl]-L-glutamic acid (5-deaza-5-oxoaminopterin), i.e., a compound having the formula:

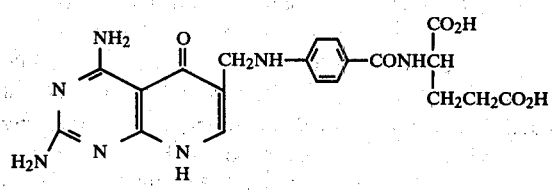

was reported by A. Srinivasan and A. D. Broom, J. Org. Chem., 45, 3746 (1980). In addition, N-[4-[(2-amino-4(3H)-oxo-10-formylpyrido[2,3-d]-pyrimidin-6-yl)methylamino]benzoyl]-L-glutamic acid (5-deaza-10-formylfolic acid), characterized only by spectral data, was reported to be formed from 5-deazafolate and formic acid by G. K. Smith, W. T. Mueller, P. A. Benkovic and S. J. Benkovic, Biochemistry, 20, 1241 (1981). A method for preparing 5-deazafolate is not disclosed.

The inhibition of bacterial dihydrofolate reductase by pyrido[2,3-d]pyrimidines has been summarized in the Advan. Heterocycl. Chem. reference. Recently, a pyrido[2,3-d]pyrimidine derivative was reported to be a potent lipid-soluble inhibitor of mammalian dihydrofolate reductase by E. M. Grivsky, S. Lee, C. W. Sigel, D. S. Duch and C. A. Nichol, J. Med. Chem., 23, 327 (1980). This reference discloses the compound:

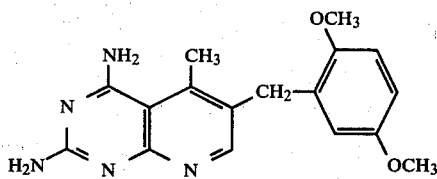

Other derivatives of this ring system have been evaluated for antihypertensive activity. Thus, L. R. Bennett et al, J. Med. Chem., 24, 382 (1981) reported that the following compound lowered blood pressure in the hypertensive rat:

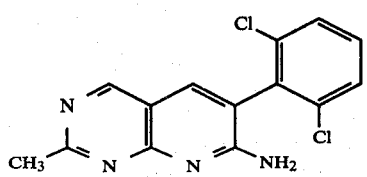

The synthesis of 5-deazafolic acid has been reported by D. T. Hurst, "An Introduction to the Chemistry and Biochemistry of Pyrimidines, Purines, and Pteridines," John Wiley and Sons, Ltd., 231 (1980). The synthesis of this compound using as an intermediate 2-amino-6-formyl-5-deazapteridine-4(3H)-one, i.e., a compound having the formula:

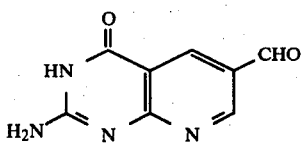

has been proposed by C. Temple, Jr. and J. A. Montgomery, "Synthesis of Potential Anticancer Agents," Cancer Chemotherapy National Service Center, Southern Research Institute Report 85, pages 1 and 2 (1966) and Report 86, pages 8 and 10 (1967). The synthesis of 5-deazafolic acid via a condensation reaction involving triformylmethane has been reported by C. P. Tseng, *Dissertation Abstracts Int. B,* 40, 3752 (1980). The thesis upon which this abstract was based, C. P. Tseng, *Studies in Heterocyclic Chemistry,* 171–185 (1979) also describes unsuccessful work on the preparation of 5-deaza-2,4-diaminopteridine-6-carboxaldehyde dimethyl acetal, i.e., a compound having the formula:

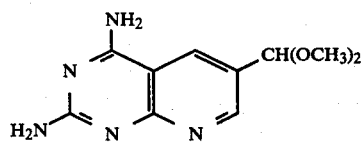

the synthesis of 5-deaza-6-formylpterin; and the conversion of this compound to 5-deazafolic acid via acetylated 5-deaza-6-formylpterin. The preparation of 5-deazaaminopterin via a long sequence of reactions involving the elaboration of a pyrimidine intermediate has been described by E. F. Elslager and J. Davoll, "Lectures in Heterocyclic Chemistry," 2, S-97, S-119–S-121 (1974).

SUMMARY OF THE INVENTION

The 5-deaza analogs of folic acid, $N^{10}$-methylfolic acid, aminopterin, methotrexate and the diethyl ester of aminopterin inhibit the growth of human epidermoid carcinoma cells No. 2 and are active against leukemia in laboratory animals. The 5-deaza analogs of folic acid, $N^{10}$-methylfolic acid, aminopterin and methotrexate have the following structures:

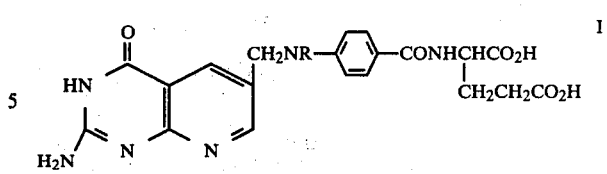

and

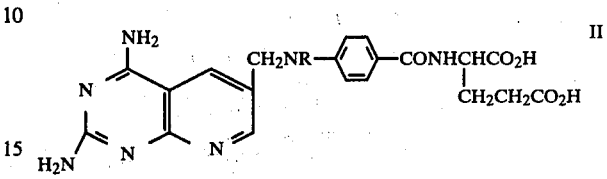

wherein R is either hydrogen or methyl.

A novel intermediate has now been found which is useful in the preparation of the compounds of Formulas I and II. This intermediate has the structure:

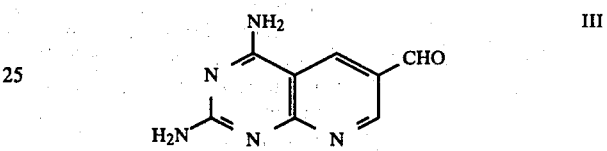

This compound is prepared by reaction of a compound having the structure:

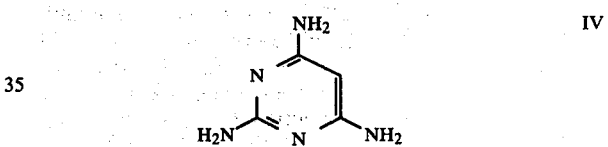

with the quaternary salt of triformylmethane (or its hydrolyzed derivatives) having the structure:

$$CH[CH=N^+(CH_3)_2]_3 \; 3X^- \qquad V$$

wherein X is a halogen atom, preferably chlorine.

Reductive alkylation of dialkyl-p-aminobenzoyl-L-glutamate having the structure:

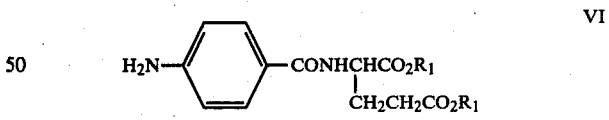

with the compounds of Formula III afforded a compound having the structure:

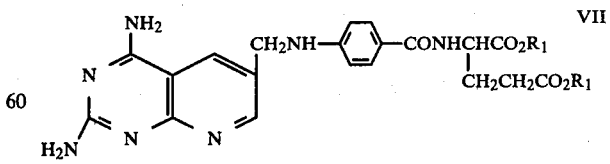

wherein $R_1$ is a lower alkyl group, i.e., a group containing up to six carbon atoms.

The compound of Formula VII was converted to the compound of Formula II (R=H) by saponification. In addition, the compound of Formula II (R=H) was treated under more drastic conditions with base to hydrolyze the 4-amino group to give the compound of Formula I (R=H). Also, methylation of II (R=H) with formaldehyde in the presence of sodium cyanoborohydride provided the compound of Formula II (R=CH$_3$). In addition, the 4-amino group of the compound of Formula II (R=CH$_3$) was hydrolyzed with base to give the compound of Formula I (R=CH$_3$). The compound of Formula I (R=CH$_3$) was also prepared by methylation of the compound of Formula I (R=H) with the formaldehyde-sodium cyanoborohydride combination.

DETAILED DESCRIPTION OF THE INVENTION

The synthesis of triformylmethane was reported by Z. Arnold and J. Zemlicka, *Coll. Czech. Chem. Commun.*, 25, 1318 (1960) and Z. Arnold, *Coll. Czech. Chem. Commun.*, 26, 3051 (1961). Thus, in one method, reaction of bromoacetic acid with the complex [(CH$_3$)$_2$N=CHCl]+Cl− resulting from treatment of N,N-dimethylformamide with phosphorus oxychloride gave a quaternary salt, probably V, which was treated with aqueous potassium carbonate to give triformylmethane. The isolation and purification of the latter is difficult, and in the procedure described herein, the intermediate quaternary salt or its hydrolyzed derivatives is used.

The condensation of V with 2,4,6-triaminopyrimidine (IV) in water at reflux gave 2,4-diaminopyrido[2,3-d]pyrimidine-6-carboxaldehyde (III). The structure of III was confirmed as described hereinafter in Example 7B by the alkaline potassium permanganate oxidation of the formyl group and hydrolysis of the 4-amino group to give the known 2-amino-4(3H)oxopyrido[2,3-d]pyrimidine-6-carboxylic acid (VIII) [R. Bernetti, F. Mancini and C. C. Price, *J. Org. Chem.*, 27, 2863 (1962); D. M. Mulvery, S. G. Cottis and H. Tieckelmann, *J. Org. Chem.*, 29, 2903 (1964)]. An authentic sample of VIII was prepared as described hereinafter in Example 7A by alkaline potassium permanganate oxidation of 2-amino-6-methyl-4(3H)oxopyrido[2,3-d]-pyrimidine, which was synthesized by the method of E. Stark and E. Breitmaier, *Tetrahedron*, 29, 2209 (1973). It has been established that in the 2,4-diaminopyrido[2,3-d]pyrimidine ring system, the 4-amino function undergoes alkaline hydrolysis readily [R. Tratner, G. Elion, G. Hitchings, and D. Sharefkin, *J. Org. Chem.*, 29, 2674 (1964)].

Although the mechanism of the condensation reaction is unknown, two of the formyl groups or potential formyl groups of V must react with the enamine moiety of the 4-aminopyrimidine with the elimination of either water or dimethylamine. The initial reaction involves the electrophilic attack of one formyl group or derivative either with the 5-position of the pyrimidine ring or with the 4-amino group to give a Schiff base followed by cyclization of the resulting monocyclic intermediate to give the desired bicyclic ring system. In the *J. Org. Chem.* reference above, Price et al. observed that pyrido[2,3-d]pyrimidines were readily formed under mild conditions from 4-aminopyrimidines and malondialdehydes containing electron-withdrawing groups. Compound V can be considered a malondialdehyde derivative substituted with an electro-withdrawing group.

Reductive alkyation of diethyl p-aminobenzoyl-L-glutamate with III and hydrogen in 70% acetic acid containing Raney nickel gave a 32% yield of 5-deazaaminopterin diethyl ester. Saponification of the ester groups in a mixture of dimethyl sulfoxide-water at ambient temperature gave an 87% yield of 5-deazaaminopterin (II, R=H). Methylation of the latter compound was accomplished by treatment of II (R=H) with formaldehyde and sodium cyanoborohydride in aqueous solution at pH 6.4 to give an 85% yield of 5-deazamethotrexate (II, R=CH$_3$). The structure of II (R=CH$_3$) was established as described hereinafter in Example 7C by oxidation with alkaline potassium permanganate to give the previously prepared 2-amino-4(3H)-oxopyrido[2,3-d]pyrimidine-6-carboxylic acid (VIII), which indicated that methylation had occurred either on the 4- or 10-amino group. Methylation of the 4-amino group was eliminated from consideration by alkaline hydrolysis of the 4-amino group to give 5-deaza-10-methylfolic acid (I, R=CH$_3$).

The preferred route for the preparation of I (R=H) involved the hydrolysis of 5-deazaaminopterin diethyl ester in aqueous sodium hydroxide at reflux temperature, which resulted in replacement of the 4-amino group as well as hydrolysis of the ester functions to give a 79% yield of 5-deazafolic acid (I, R=H). Methylation of the compound of Formula I (R=H) with formaldehyde and sodium cyanoborohydride gave an 84% yield of 5-deaza-10-methylfolic acid (I, R=CH$_3$), which was identical to that prepared by the alkaline hydrolysis of the compound of Formula II (R=CH$_3$). The structures of I (R=H and CH$_3$), II (R=H and CH$_3$), and 5-deazaaminopterin diethyl ester were confirmed by elemental analyses, $^1$H-NMR and mass spectral data.

The following examples illustrate the best modes known for carrying out this invention:

EXAMPLE 1

2,4-Diaminopyrido[2,3-d]pyrimidine-6-carboxaldehyde (III)

Phosphorus oxychloride (27.5 ml, 46.0 g, 300 mmol) was added over 15 minutes with stirring to N,N-dimethylformamide (11.0 g, 150 mmol), which was cooled with an ice bath. After stirring at room temperature for 1 hour, the reaction mixture was treated with bromoacetic acid (13.9 g, 100 mmol). The resulting solution, protected by a calcium chloride tube was heated at 92° C. for 10 hours and evaporated to dryness in vacuo. The colored oil (~30 g) was dissolved in water (1000 ml), and the solution was neutralized with 50% sodium hydroxide to pH 7. After addition of 2,4,6-triaminopyrimidine (5.00 g, 40.0 mmol), the solution was refluxed for 3 hours and filtered hot through a fluted filter. The filtrate was cooled and the solid that precipitated was collected by filtration and dried in vacuo over P$_2$O$_5$: yield, 2.53 g (33%). Mass spectrum, m/e 189 (M+). HPLC [0.1 M NH$_4$OAc (pH 3.6) —CH$_3$OH (9:1)] indicated that this product was 86% pure. A sample (200 mg) was dissolved in 0.1 N HCl (15 ml) and diluted with acetone (225 ml) to precipitate impure III: yield, 91 mg. The filtrate was evaporated to dryness under reduced pressure and the residue was dried in vacuo over P$_2$O$_5$ to give compound III: yield, 128 mg; mp, gradual darkening and decomposition with white sublimate when taken to 360° C. $\lambda_{max}$nm ($\epsilon \times 10^{-3}$): 0.1 N HCl —258 (16.4), 317 (9.12), 326 sh (8.42); pH 7–263 (15.0), 316 (10.1), 345 (10.8); 0.1 N NaOH —254 (13.2), 267 (13.5), 3.16 (8.56), 347 (10.0). $^1$H-NMR (CF$_3$CO$_2$D, 6% w/v), 9.48 s, 9.75 s (5 —CH, 7 —CH), 10.21 s (6 —CHO).

Anal. Calcd for C$_8$H$_7$N$_5$O.HCl.1.3H$_2$O: C, 38.57; H, 4.30; N, 28.12. Found: C, 38.44; H, 4.15; N, 28.14.

EXAMPLE 2

Diethyl N-[4-[(2,4-diaminopyrido[2,3-d]pyrimidin-6-yl)methylamino]benzoyl]-L-glutamate (VII; $R_1=C_2H_5$)

A solution of compound III (1.47 g, 5.90 mmol) in warm 70% acetic acid (59 ml) was cooled to 25° C., treated with diethyl p-aminobenzoyl-L-glutamate (2.28 g, 7.08 mmol) and hydrogenated in the presence of Raney nickel (6.3 g, weighed wet) at 25° C. and atmospheric pressure for 17 hours. The mixture was filtered and the catalyst was washed with 70% acetic acid (25 ml). The combined filtrate and wash was evaporated to dryness under high vacuum, and a solution of the residue in ethanol was filtered into 2 N $Na_2CO_3$ (60 ml). The mixture was stirred to give a homogeneous powder which was collected, washed with water and dried. A solution of the resultant powder in boiling ethanol (415 ml) was filtered hot and evaporated to dryness in vacuo. The residue was triturated with $CHCl_3$ (85 ml), collected by filtration and the solid was washed with additional $CHCl_3$ (40 ml). A suspension of the solid in boiling ethanol (140 ml) was stirred for 20 minutes and refrigerated. The product was collected by filtration and dried in vacuo ($P_2O_5$): yield 945 mg (32%), mp 262° C. (Kofler Heizbank). Mass spectrum, m/e 496 $(M+1)^+$; $\lambda_{max}$nm ($\epsilon \times 10^{-3}$); 0.1 N HCl —218 (42.4), 280 sh (19.3), 300 (22.0); pH 7—218 (36.4), 249 (20.2), 280 sh (22.3), 297 (23.6), 355 sh (6.10); 0.1 N NaOH —249 (22.0), 280 (23.8), 297 sh (22.5), 345 (7.23); $^1$H-NMR(DMSO-$d_6$, 6% w/v), $\delta$ 1.18 m ($CH_3$), 2.05 m ($CH_2CH_2CO$), 2.43 t ($CH_2CO$), 4.08 m ($CH_2O$), 4.32 m ($CH_2N$, CHN), 6.31 s, 7.51 s ($NH_2$), 6.67 d, 7.69 d ($C_6H_4$), 6.71 s ($CH_2N\underline{H}$), 8.25 d (CONH), 8.41 d (5 —CH, J=2.0 Hz), 8.66 d (7-CH, J=2.0 Hz).

Anal. Calcd for $C_{24}H_{29}N_7O_5$: C, 58.17; H, 5.90; N, 19.79. Found: C, 57.91; H, 6.24; N, 19.55.

Evaporation of the filtrate and trituration of the residue with ethanol gave an additional 123 mg of less pure product, mp 246° C.

EXAMPLE 3

N-[4-[(2-Amino-4(3H)-oxopyrido[2,3-d]pyrimidin-6-yl)methylamino]benzoyl]-L-glutamic Acid (I, R=H)

A suspension of the product obtained in the previous example, VII ($R_1=C_2H_5$) (100 mg, 0.202 mmol) in $O_2$ free 1 N NaOH (4 ml) was stirred at reflux temperature under $N_2$ for 4.25 hours and acidified to pH 3.1 with 6 N HCl. The precipitate was collected by filtration and dried in vacuo. A solution of the solid in 1 N HCl (0.5 1 ml) was diluted with water (0.5 ml), filtered, diluted with water (9 ml) and adjusted to pH 3.1 with 1 N NaOH. The precipitate was collected by filtration, washed with water at pH 3.1 and dried in vacuo ($P_2O_5$): yield 74 mg (79%), mp indefinite; mass spectrum, m/e 441 $(M+1)^+$; $\lambda_{max}$nm ($\epsilon \times 10^{-3}$): 0.1 N HCl —213 (37.0), 280 (23.9), 297 sh (20.6), 350 (7.35); pH 7—216 (40.8), 278 (24.9), 295 sh (23.8); 0.1 N NaOH —243 (22.9), 278 (24.0), 295 sh (22.7), 345 sh (7.58); $^1$H-NMR ($CF_3CO_2D$, <6% w/v), 2.56 ($C\underline{H}_2CH_2CO$), 2.82 t ($CH_2CO$), 5.11 m (CHN, $CH_2N$), 7.87 d, 8.15 d ($C_6H_5$), 8.98 s, 9.10 s (5 —CH, 7 —CH).

Anal. Calcd for $C_{20}H_{20}N_6O_6 \cdot 1.1H_2O$: C, 52.20; H, 4.86; N, 18.26. Found: C, 52.00; H, 4.92; N, 18.54.

EXAMPLE 4

N-[4-[(2,4-diaminopyrido[2,3-d]pyrimidine-6-yl)methylamino]benzoyl]-L-glutamic acid (II, R=H)

A solution of the product obtained in Example 2, VII ($R_1=C_2H_5$) (359 mg, 0.724 mmol) in dimethyl sulfoxide (10 ml) under $N_2$ was treated with 1 N NaOH (1.81 ml, 1.81 mmol), stirred in a stoppered flask under $N_2$ for 6 hours, and evaporated to dryness in vacuo at <30° C. A solution of the residue in water (18 ml) was filtered and acidified to pH 3.6 with 1 N HCl. The precipitate was collected by filtration, washed with water at pH 3.6 and dried in vacuo ($P_2O_5$); yield 297 mg (87%), mp indefinite (softens above 200° C.); mass spectrum, m/e 440 $(M+1)^+$; $\lambda_{max}$nm ($\epsilon \times 10^{-3}$): 0.1 N HCl —218 (40.5), 280 sh (16.9), 300 (18.8); pH 7—218 (38.5), 2.45 (19.2), 280 (23.9), 296 sh (22.7); 0.1 N NaOH —248 (22.0), 280 (24.4), 296 sh (22.7), 345 (7.75); $^1$H-NMR (DMSO-$d_6$, 6% w/v), $\delta$2.00 m ($C\underline{H}_2CH_2CO$), 2.29 t ($CH_2CO$), 4.36 m (CHN, $CH_2N$), 6.66 d, 7.68 d ($C_6H_4$), 7.41 ($NH_2$), 8.04 m ($NH_2$, NH, $CO_2H$), 8.52 d, 8.70 d (5 —CH, 7 —CH).

Anal. Calcd for $C_{20}H_{21}N_7O_5 \cdot 1.9H_2O$: C, 50.72; H, 5.28; N, 20.70. Found: C, 50.86; H, 5.43; N, 20.50.

EXAMPLE 5

N-[4-[[(2,4-Diaminopyrido[2,3-d]pyrimidin-6-yl)methyl]methylamino]benzoyl]-L-glutamic acid (II, R=$CH_3$).

A suspension of compound II (R=H) (100 mg, 0.211 mmol) in $O_2$ free water (5 ml) under $N_2$ was adjusted to pH 6.4 with 1 N NaOH to give a solution which was treated with 38% HCHO (83.1 μl, 1.14 mmol) followed by $NaBH_3CN$ (19.9 mg, 0.317 mmol). The solution was maintained at pH 6.4 by gradual addition of 1 N HCl over a period of 45 minutes. The solution was stirred under $N_2$ for 23 hours, filtered and acidified to pH 3.6 with 1 N HCl. The product was collected by filtration, washed with water at pH 3.6 and dried in vacuo ($P_2O_5$): yield 97 mg (94%), mp indefinite (softens and darkens above 217° C.); mass spectrum, m/e 454 $(M+1)^+$; $\lambda_{max}$nm ($\epsilon \times 10^{-3}$): 0.1 N HCl —221 (37.1), 311 (19.0); pH 7-219 (35.1), 247 (18.1), 305 (25.2); 0.1 N NaOH —249 (19.9), 305 (25.0), 355 sh (6.15); $^1$H-NMR (DMSO-$d_6$, <5% w/v), $\delta$2.00 m ($C\underline{H}_2CH_2CO$), 2.28 t ($CH_2CO$), 3.12 s ($CH_3$), 4.32 m (CHN), 4.64 s ($CH_2N$), 6.78 d, 7.72 d ($C_6H_4$), 8.31 d (5 —CH), 8.59 d (7 —CH).

Anal. Calcd for $C_{21}H_{23}N_9O_5 \cdot 2H_2O$: C, 51.53; H, 5.56; N, 20.03. Found: C, 51.54; H, 5.47; N, 20.35.

EXAMPLE 6

N-[4-[[(2-Amino-4(3H)-oxopyrido[2,3-d]pyrimidin-6-yl)methyl]methylamino]benzoyl]-L-glutamic Acid (I, R=$CH_3$)

A. A suspension of I (R=H)(60 mg, 0.13 mmol) was methylated by the procedure used for the preparation of II (R=$CH_3$). The reaction solution after filtration was diluted with oxygen free water (3 ml) and acidified to pH 3.1 with 1 N HCl. The product was collected, washed with water at pH 3.1 and dried in vacuo ($P_2O_5$); yield 53 mg (84%), mp indefinite; mass spectrum, m/e 455 $(M+1)^+$; $\lambda_{max}$nm ($\epsilon \times 10^{-3}$): 0.1 N HCl —215 (35.1), 280 (19.0), 306 (20.8), 355 sh (6.85); pH 7–216 (38.0), 274 (19.0), 306 (27.3); 0.1 N NaOH —242 (22.9), 275 sh (17.4), 307 (25.4); $^1$H-NMR (DMSO-$d_6$, 5% w/v), $\delta$ 2.02 m ($C\underline{H}_2CH_2CO_2H$), 2.35 t ($CH_2CO$), 3.09 s (CH$_3$), 4.37 m (CHN), 4.73 s (CH$_2$N), 6.82 d, 7.75 d (C$_6$H$_4$), 8.03 d (5 —CH), 8.19 d (NH), 8.55 d (7 —CH).

Anal. Calcd for C$_{21}$H$_{22}$N$_6$O$_5$·H$_2$O·0.75 HCl: C, 52.14; H, 5.16; N, 17.37. Found: C, 52.12; H, 5.12; N, 17.47.

B. A solution of compound II (R=CH$_3$)(50 mg) was hydrolyzed by the procedure of Example 3 for the preparation of compound I (R=H) to give a 64% yield of compound I (R=CH$_3$). HPLC and uv data indicated that this product was identical to that prepared in A above.

EXAMPLE 7

2-Amino-4(3H)-oxopyrido[2,3-d]pyrimidine-6-carboxylic Acid (VIII)

A. To a solution of 2-amino-6-methyl-4(3$\underline{H}$)-oxopyrido[2,3-d]pyrimidine (177 mg, 1.00 mmol) in 1 N NaOH (60 ml) at reflux temperature was added with stirring an aqueous solution of 0.2 M potassium permanganate over a period of about 1 hour. After the excess permanganate was destroyed with sodium bisulfite, the resulting hot mixture was filtered through Celite. The filtrate was adjusted to ~pH 3 with HCl and allowed to stand to room temperature for 18 hours. The solid that precipitated (170 mg) was collected by filtration, dissolved in 2 N NaOH, and the solution was cooled to deposit the sodium salt of the product. The salt was collected by filtration, dissolved in water, and the solution was adjusted to pH 2–3 with HCl. The solid that deposited was collected by filtration and dried in vacuo over P$_2$O$_5$: yield, 67 mg (29%); mp>264° C. HPLC [0.1 M Na$_2$HPO$_4$ (pH 7) —CH$_3$CN (92:8)] showed that this sample was homogeneous. $\lambda_{max}$nm ($\epsilon \times 10^{-3}$): 0.1 N HCl —216 (35.9), 266 (14.5), 306 (6.70), 315 sh (5.35); pH 7–216 (26.8), 232 sh (17.8), 283 (11.4), 310 sh (5.93), 321 sh (5.37); 0.1 N NaOH —246 (22.8), 292 (10.1), 332 (7.20). $^1$H-NMR (NaOD, 5% w/v), δ 8.76 d (7 —CH, J=1.5 Hz), 9.06 d (5 —CH).

Anal. Calcd for C$_8$H$_6$N$_4$O$_3$·0.6HCl: C, 42.13; H, 2.92; N, 24.57. Found: C, 42.04; H, 2.80; N, 24.41.

B. Treatment of 2,4-diaminopyrido[2,3-d]pyrimidine-6-carboxaldehyde (III) (186 mg, ~0.980 mmol) by the procedure described in A resulted in hydrolysis of the 4-amino group and oxidation of the formyl group to give VIII: yield, 158 mg; Field desorption mass spectrum, m/e 206 (M$^+$). The HPLC chromatogram (co-injection) of this product was identical with that of compound VIII prepared in A.

C. A solution of N-[4-[[(2,4-diaminopyrido[2,3-d]pyrimidin-6-yl)methyl]methylamino]benzoyl]-L-glutamic acid (II, R=CH$_3$) (5.00 mg, 0.010 mmol) in 2 ml of 1 N NaOH was treated with KMnO$_4$ (1.62 mg, 0.010 mmol), heated at 95° C. for 3 hours, filtered and adjusted to pH 8 with 1 N HCl. An HPLC chromatogram indicated the presence of XII (~22% yield) and unreacted II (R=CH$_3$) (~50% recovery). The ultraviolet spectrum (240–360 nm) of the eluted compound VIII was identical to the ultraviolet spectrum of an authentic sample.

Cell culture cytotoxicity data and activity against lymphocytic leukemia P388 in mice for compounds I, II and VII (R$_1$=C$_2$H$_5$) are set forth in Table 1.

TABLE 1

Cell Culture Cytotoxicity Data[a] and Activity Against Lymphocytic Leukemia P388 in Mice[b].

| Compound | ED$_{50}\mu$M[c] | P388[d] dose, mg/kg | % ILS |
|---|---|---|---|
| I(R = H) | 6.1 | 100 | 17 |
| I(R = CH$_3$) | 11.2 | 200 | 11 |
| II(R = H) | 0.013 | — | — |
| II(R = CH$_3$) | 0.004 | 4 | 97[e] |
| VIII(R$_1$ = C$_2$H$_5$) | 0.052 | 2 | Toxic |
| Methotrexate | 0.001 | 2 | 61[f] |

[a]Human epidermoid carcinoma cell No. 2. R. I. Geran, N. H. Greenberg, M. M. MacDonald, A. M. Schumacher, and B. J. Abbott, Cancer Chemotherapy Reports, Part 3, Vol. 3 (No. 2), 1971.
[b]Reference in a.
[c]Concentrations inhibiting colony formation by 50% after 12 days as determined in plastic flask. L. L. Bennett, Jr., H. D. Schnetti, N. H. Vail, P. W. Allan, and J. A. Montgomery, Mol. Pharmacol., 2, 432 (1966).
[d]CDF$_1$ mice inoculated with 10$^6$ P388 cells intraperitoneally; drug administered intraperitoneally on qd 1–5 days.
[e]One 30th-day survivor.
[f]Administered intraperitoneally on qd 1–9 days.

We claim:

1. 2,4-Diaminopyrido[2,3-d]pyrimidine-6-carboxaldehyde.

* * * * *